United States Patent [19]

Iglesia et al.

[11] Patent Number: 5,036,032
[45] Date of Patent: Jul. 30, 1991

[54] SELECTIVE CATALYSTS AND THEIR PREPARATION FOR CATALYTIC HYDROCARBON SYNTHESIS

[75] Inventors: Enrique Iglesia, Clinton; Hilda Vroman, Piscataway; Stuart Soled, Pittstown; Joseph Baumgartner, Califon; Rocco A. Fiato, Basking Ridge, all of N.J.

[73] Assignee: Exxon Research and Engineering Company, Florham Park, N.J.

[21] Appl. No.: 450,957

[22] Filed: Dec. 12, 1989

Related U.S. Application Data

[63] Continuation-in-part of Ser. No. 323,077, Mar. 14, 1989, abandoned, which is a continuation of Ser. No. 173,263, Mar. 25, 1988, abandoned.

[51] Int. Cl.[5] .................. B01J 21/12; B01J 21/06; B01J 23/70; C07C 1/04
[52] U.S. Cl. .................. 502/260; 518/715; 502/325; 502/328; 502/332; 502/350
[58] Field of Search .................. 502/260, 325, 350; 518/715

[56] References Cited

U.S. PATENT DOCUMENTS

| | | | |
|---|---|---|---|
| 2,223,777 | 12/1940 | Beeck et al. | 502/325 |
| 2,512,608 | 6/1950 | Buchmann | 502/336 |
| 2,696,475 | 12/1954 | Farrow | 502/325 |
| 4,568,663 | 2/1986 | Mauldin | 502/325 |
| 4,599,481 | 7/1986 | Post et al. | 585/700 |
| 4,605,676 | 8/1986 | Kobylinski et al. | 502/335 |
| 4,637,993 | 1/1987 | Van Erp et al. | 502/242 |
| 4,916,108 | 4/1990 | McLaughlin et al. | 502/325 |

FOREIGN PATENT DOCUMENTS 0266898  5/1988  European Pat. Off. ............ 502/325

Primary Examiner—Paul E. Konopka
Attorney, Agent, or Firm—Sidney Persley; Jay Simon

[57] ABSTRACT

Supported catalysts for Fischer-Tropsch processes prepared by contacting a suitable support with a catalyst in the form of a metal salt and depositing the catalyst on the support. Where rim type catalyst are preferred, a molten salt starting material is used. For non-rim type catalyst, such as powdered catalyst, solution salt starting materials may be used. The catalyst is prepared without high temperature calcination of the catalyst before reduction by reducing the salt directly on the support to the metal. During the reduction step, the heating rate is a slow single steady heating rate.

12 Claims, 3 Drawing Sheets

SELECTIVE CATALYSTS AND THEIR PREPARATION FOR CATALYTIC HYDROCARBON SYNTHESIS

This application is a Continuation-in-Part of Ser. No. 323,077, filed March 14, 1989, which is a Rule 62 Continuation of U.S. Ser. No. 173,263, filed March 25, 1988, both now abandoned.

BACKGROUND OF THE INVENTION

1. Field of the Invention

This invention relates to improved catalysts, their manufacture, and use in hydrocarbon synthesis, Fischer-Tropsch type reactions, to prepare heavy hydrocarbons, $C_{5+}$, from synthesis gas, carbon monoxide and hydrogen.

2. The Prior Art

Hydrocarbon synthesis, Fischer-Tropsch, reactions involving the reaction of carbon monoxide and hydrogen over a catalyst, to produce heavier hydrocarbons, $C_5+$, are diffusion limited. Hydrogen diffuses at a faster rate into the catalyst particle than carbon monoxide and the $H_2/CO$ ratio at any point below the exterior profile of the catalyst will be greater than the hydrogen to carbon monoxide ratio in the bulk gas. As the reactants, hydrogen and carbon monoxide, proceed further into the catalyst particle towards its center, the ratio of hydrogen to carbon monoxide will continue to increase as long as the catalyst metal sites of the catalyst are available to consume $H_2$ and CO.

The stoichiometric consumption ratio of hydrogen and carbon monoxide to produce heavy hydrocarbons is 2.1/1. Ratios above the stoichiometric ratio favor increasing formation of methane, $CH_4$. However, methane is not a desirable product of the hydrocarbon synthesis reaction, although the synthesis gas is often prepared from methane, for example, by partial oxidation or catalytic reforming.

Various methods for overcoming the diffusion limitation phenomenon of hydrocarbon synthesis catalysts have been developed in the prior art, one of which is the coated or rim-type catalysts. Examples of coated or rim type catalysts are U.S. Pat. Nos. 2,512,608 and 4,599,481, and 4,637,993. The latter two patents disclose cobalt or promoted cobalt catalysts on supports which may be silica, alumina, or silica-alumina. Other examples of rim-type catalysts appear in Everson et al, Fischer-Tropsch Reaction Studies with Supported Ruthenium Catalysts, Journal of Catalysis, 53, 186–197 (1978) and Dixit and Tavlarides, Kinetics of the Fischer-Tropsch Synthesis, Ind., Eng. Chem. Proc. Des. Dev. 1983, 22, 1–9, where various metals such as cobalt, ruthenium, and iron are disclosed as hydrocarbon synthesis catalysts and a coated ruthenium on alumina catalyst is utilized in hydrocarbon synthesis rate studies. The catalyst has a rim of about 300 um in thickness.

The use of coated or rim type catalysts has been successful in limiting methane formation and increasing $C_5+$ yields in hydrocarbon synthesis reactions. However, the preparation of rim type catalysts is relatively difficult and the use of available catalyst metal atoms as sites for promoting the desired reactions has not necessarily been efficient.

In addition, during the reduction of the catalyst metal presursor, which typically requires heating in the presence of a reducing agent, the catalyst precursor is not heated at a single steady heating rate. In the prior art, heating is carried out over a broad range of temperatures for a specified time to maximum temperature. For example, Farrow et al U.S. Pat. No. 2,696,475 teaches a method for preparing nickel, cobalt or copper catalyst using a hydrogen reducing agent. The catalyst precursor is heated from 300° C. to 500° C. for about 4 hours. In Mauldin U.S. Pat. No. 4,568,663 a rhenium promoted cobalt catalyst precursor is reduced at temperatures ranging from 250° C. to 500° C. for periods ranging from 0.5 to 24 hours. In neither case is a particular heating rate for the catalyst precursor material specified.

The rate of heating during reduction later became more important after it was recognized that the reduction of the catalyst metal precursor to improve catalyst activity was temperature path dependent. However, these processes either employ a multiplicity of heating rates or calcine the catalyst at high temperatures before the reduction step. Reducing the catalyst metal precursor directly, without calcination, was then known to result in catalysts having inferior activity than that of catalysts produced by a process that employs a calcination step.

For example, Eri et al U.S. Pat. No. 4,801,573, shows a method for preparing a rhenium and cobalt catalyst on a support. The reduction is carried out at the single steady rate of 1° C./min. to the maximum temperature of 350° C. However, the process requires calcination of the catalyst precursor before reduction. Koblinski et al U.S. Patent 4,605,676, reveals a process for directly reducing cobalt catalyst precursors without calcining. The catalyst precursors are prepared from cobalt nitrate solutions and cobalt carbonyls on alumina based supports. During the reduction step, the heating rate is held steady at 1° C./min. to 350° C. For comparative purposes, the directly reduced catalyst (R350) was subjected to an additional oxidation and reduction step to produce a second catalyst (ROR). Koblinski teaches that the catalyst prepared by the ROR procedure has much higher activity than catalyst prepared by direct reduction (R350) at a heating rate of 1° C./min.

Beuther et al In U.S. Pat. No. 4,493,905, gas synthesis catalysts are prepared by directly reducing the catalyst from a catalyst metal salt. Although calcination was omitted, the reduction was carried out by a multiple of heating steps of different rates, each to a different maximum temperature. For instance, in one embodiment, the catalyst is initially heated at 1° C./min. up to 100° C. and held at that temperature for about 1 hour and then heated at 1° C./min. up to 200° C. and held at that temperature for about 2 hours and finally, heated at 10° C./min. up to 360° C. and held at that temperature for 16 hours.

We have now discovered a method for preparing coated or rim type catalysts having a relatively uniform rim of predictable thickness and wherein the efficiency of the catalyst metal atoms and promotion of desired reactions is greatly enhanced. Furthermore, we have discovered a process whereby catalyst dispersion and activity can be increased by directly reducing a catalyst metal precursor, in the form of a salt, in the presence of a reducing agent where heating during the reduction is a single steady heating rate up to a maximum temperature. The process is applicable to rim type as well as non-rim type catalysts, e.g., powdered catalyst.

SUMMARY OF THE INVENTION

In one aspect, the invention relates to the preparation of coated or rim type catalysts where substantially all of the catalyst metal is located in the rim or coating on the exterior portion of a catalyst particle and relatively little or none of the catalyst metal is located towards the center of the catalyst particle. In another aspect, the invention relates to a process for manufacturing hydrocarbon synthesis catalysts where the catalyst metal is reduced directly from the starting material. The novel process disclosed herein for preparing hydrocarbon synthesis catalyst provides many advantages such as: (a) the capability of being carried out in fewer process steps than previous processes, (b) eliminating the need for high temperature calcination of the catalyst metal precursor before reduction, (c) eliminating the need to expose the catalyst to further high temperature oxidation or reduction after the initial reduction and (d) avoids the need to reduce the catalyst precursor more than once. The process applies equally well for rim as well as non-rim type catalysts.

The catalyst may be prepared by melt impregnation or incipient wetness techniques. In either case, the catalyst metal is directly reduced to the metal from a salt starting material. As such, the normal calcining step between drying and the initial reduction is eliminated and any subsequent oxidation or reduction steps are not needed to achieve a catalyst of high dispersion and activity. Furthermore, because site density is a function of catalyst metal dispersion, high temperature calcination of the dried, impregnated catalyst which produces agglomeration is therefore avoided.

DESCRIPTION OF THE FIGURES

FIG. 7 has a scale that shows not only that the rim is very clearly defined by thickness but that the rim is about 150 um in thickness.

DETAILED DESCRIPTION

Figure 1:
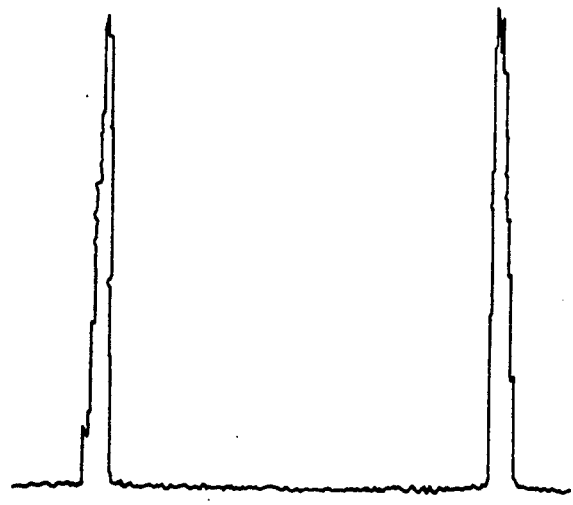
FIGS. 1 through 3 are photomicrographs of a cross section of a $Co/SiO_2$ catalyst prepared in accordance with the preferred process of this invention by the procedure outlined below under Experimental Procedures B. Cobalt Distributions.
Figure 2:
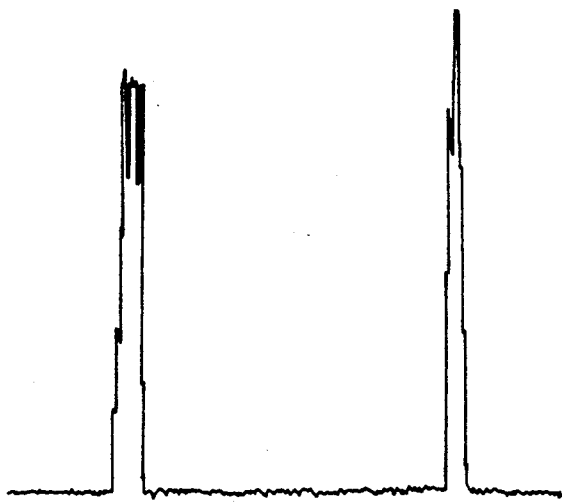
Figure 3:
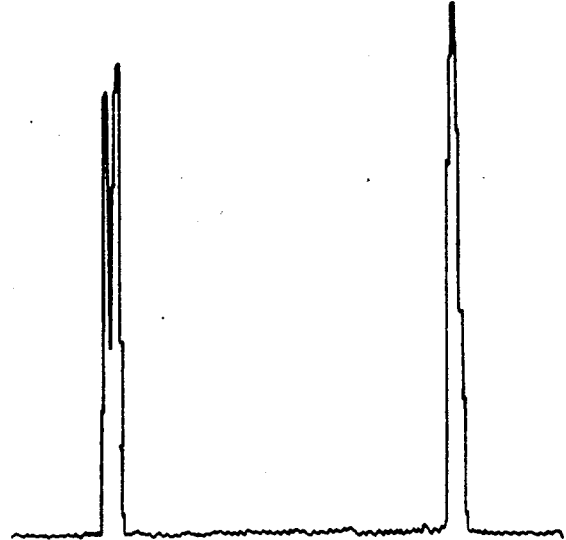
Figure 4:
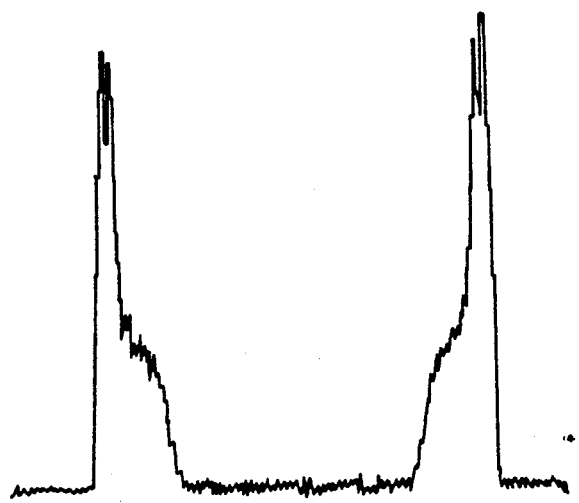
FIGS. 4 through 6 are similarly obtained photomicrographs of $Co/Zr/SiO_2$ catalyst prepared by the method disclosed in U.S. Pat. No. 4,599,481.
Figure 5:
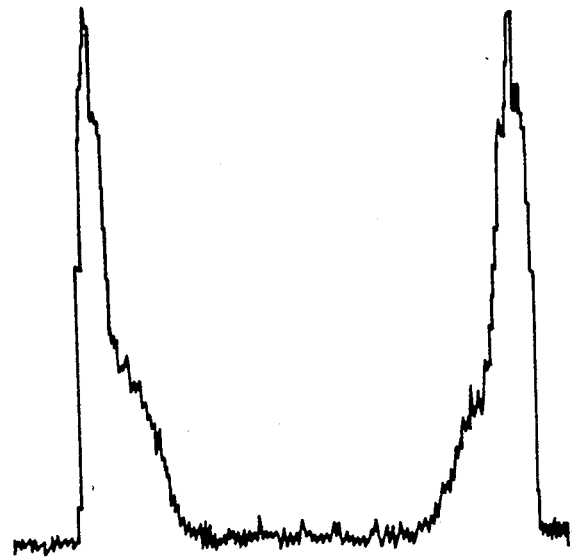
Figure 6:
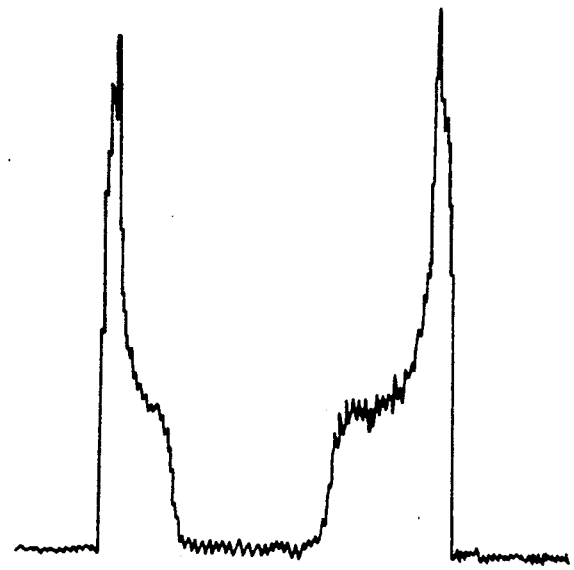
Figure 7:
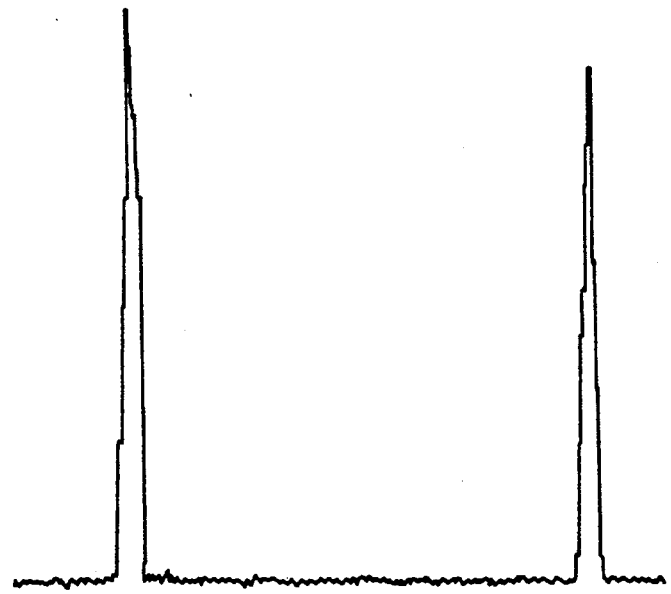
FIGS. 7 and 8 are similarly obtained photomicrographs of catalyst E and catalyst F described below and prepared by the method of this invention.
Figure 8:
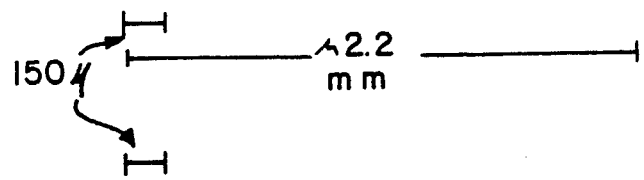
Figure 8:
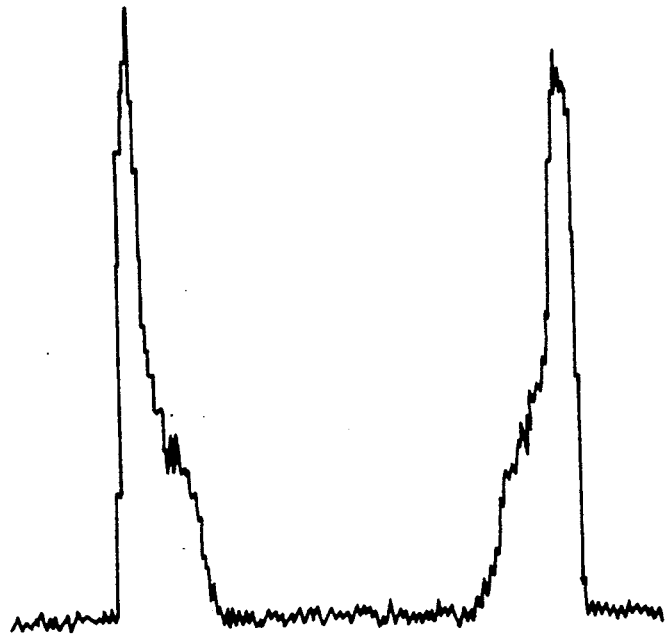

The hydrocarbon synthesis, Fischer-Tropsch, reaction is well known and the operating conditions for it have been well described in many publications. In general, temperatures may range from about 160° to 300° C., preferably about 190° C. to 260° C. while pressures may vary widely, e.g., above about 80 psig, preferably about 80 psig to 600 psig, more preferably about 140 psig to 400 psig. The gas hourly space velocity can range from about 100 v/hr/v to about 5,000 v/hr/v, preferably about 300 to 1,500 v/hr/v. The hydrogen to carbon monoxide ratio may range widely, for example, at least about 0.5/1 to as high as 10/1, preferably about 0.5/1 to 4/1 and more preferably about 1/1 to 2.5/1. With the catalyst of this invention, lower hydrogen to carbon monoxide ratios, that is, less than about 1.7/1 or about 1.5/1 to 1.7/1 have been found particularly effective.

Catalyst site density, as defined herein, is the number of catalyst surface atoms [sites] per catalyst volume. Site density may be qualitatively defined as the number of sites per unit volume in the catalyst promoting the reaction between hydrogen and carbon monoxide to from $C_5+$ hydrocarbons. Quantitatively, site density is defined herein as $$\frac{A}{B} \times D \times g$$

wherein A is the number of grams of catalyst metal per gram of catalyst, g Co/gm cat; B is the molecular weight of the catalyst metal, g/g-atom; D is dispersion, g-atom surface catalyst metal/g-atom total catalyst metal, as determined by hydrogen chemisorption; and g is the specific gravity of the catalyst (support+catalyst metal), g/liter.

Catalytic metals for Fischer-Tropsch reactions have been widely reported as cobalt, ruthenium, iron and nickel. However, when making rim-type catalyst cobalt is the preferred metal and is employed in amounts of about 5 to 50 wt. % of the catalyst, and preferably in amounts of about 7 to 30 wt. %. Promoters may be employed such as zirconium and, if employed, used in amounts ranging from 0.1 to 10 wt. % of catalyst.

The hydrocarbon synthesis reaction may be carried out in either fixed-bed, trickle-bed, slurry or fluid bed systems. In a fixed-bed system, catalyst pellets of 0.5–3 mm effective diameter as spheres or cylinders are loaded into a tube and synthesis gas is passed into the tube for conversion to heavy hydrocarbons as liquids. The hydrocarbons produced are $C_5+$, preferably $C_{10}$ to $C_{40}$ and higher, preferably substantially paraffinic. Large pellets are needed in fixed-bed reactors in order to minimize pressure drop restrictions.

The cobalt metal is supported on a carrier and, generally, inorganic refractory oxides are employed as supports. Preferred supports are silica, magnesia, alumina, silica-alumina, and titania and of these, supports having an increasing surface area are preferred relative to supports of lower surface area because the higher surface area supports stabilize higher Co dispersions. The particular preparation method of this invention permits high catalyst loadings with high dispersion levels and greater site density. Generally, higher surface area materials will permit higher catalyst loadings and dispersions. Frequently, they also provide higher pellet porosity, thus enhancing reactant diffusion rates. Preferred surface areas range from 50–500m²/g of $Al_2O_3$, $SiO_2$, carbon, $MgAl_2O_3$, $MgCr_2O_4$, $TiO_2$, substituted titanias, etc.

A key aspect in the preparation of rim type catalyst is the use of a cobalt source of sufficient viscosity and at loading conditions, to prevent capillary action within the support material from pushing the cobalt salt into the interior regions of the support.

By virtue of the invention, a catalyst can be prepared that has a well defined rim, that is, where the cobalt is virtually completely located in a narrow band on the outer surface of the particle. In contrast to catalysts prepared by other methods, e.g., dipping from a solution, virtually none of the cobalt migrates to the interior of the catalyst particle. See, for example, FIGS. 4, 5, 6, and 8 which are examples of a prior art dipping technique and show that cobalt is deposited well inside the catalyst particle and thereby negates to a substantial degree the rim concept for eliminating diffusion limitation problems in Fischer-Tropsch reactions.

Generally, the cobalt is concentrated in the outer portion of the support as a rim. The term coating while used herein is inappropriate because it suggests a catalyst particle where the cobalt forms a coating on the support material as opposed to a catalyst particle wherein the cobalt is deposited, either by impregnation or incipient wetness, within the internal pore structure of the support material and located near the external surface of the pellet. A better term is a rim catalyst and a coated catalyst for purposes of this invention is deemed synonymous to a rim catalyst. The thickness of the rim is important because of diffusion limitation criteria. When hydrogen diffuses through the liquid-filled pore system into the particle more quickly than carbon monoxide, the catalytic metal—cobalt—must be located close enough to the exterior surface of the particle so that it will promote the hydrocarbon synthesis reaction before the hydrogen/carbon monoxide ratio becomes so great as to affect the reaction product and lead to increased methane production.

The rim thickness should be no greater than about 300 um and rim thickness above this limit (at usual temperature, pressure, and catalyst productivities) the $H_2/CO$ ratio will be too high for maximizing the desired $C_5+$ products. Preferably, the coating or rim is less than about 200 um in thickness and more preferably about 50-150 um, wherein the site density is relatively high, for example, greater than about 0.04 g-atom surface/liter catalyst. The new rim catalyst is prepared by a novel technique that employs a catalyst metal, preferably cobalt, in liquid form, as a molten salt or molten hydrated salt, of sufficient viscosity to prevent capillary forces from driving the liquid into the interior of the support.

The composition for a rim type catalyst produced by following this invention has at least 95%, preferably at least 98% of the cobalt located on the rim. Assuming, for example, a spherical catalyst particle of 2.2 mm diameter, all of the cobalt located in a rim of 200 um will be located in a rim having a volume of 45% of the total catalyst particle volume; for 150 um rim the volume will be 35.5% and for a 100 um rim the volume will be 24.8%.

The method of preparation using a cobalt containing liquid of appropriate viscosity allows the preparation of rim catalysts of the proper rim thickness. This may result from a limited intrinsic metal ion transport rate in viscous media or may be due to the rapid crystallization and pore blocking by the cooling molten salt as it contacts the colder particles.

The desired preparation is achieved by using the molten form of a water soluble cobalt salt, for example cobalt nitrate $Co(NO_3)_2$. Cobalt nitrate may also occur as a hydrate, $Co(NO_3)_2.6H_2O$, and is a solid at room temperature. In making the rim catalyst, the salt is melted at a temperature slightly above the melting point of the salt (65° C.) but not so high as to change substantially the viscosity of the resulting liquid, e.g., about 5° to 25° C. higher than the melting point. The molten salt is preferably employed in the substantial absence of water or any other low viscosity polar or a polar protic solvent, although up to about 10 wt. % water may be tolerated, preferably less than about 5 wt. % $H_2O$, based on weight of solid salt.

The essential feature of the use of a molten salt or hydrated salt is the use of a salt, normally solid at room temperature, that melts before it decomposes. Thus, the useable temperature range of any salt in the practice of this invention is that temperature range between the melting point and the decomposition temperature. If a hydrated salt is used or if added water is present, the useful temperature range is preferably in the lower portion of the usable temperature range and minimal experimentation can further define the limits. Use of molten salts provides the appropriate viscosity to allow preparation of rim-type catalysts.

We have illustrated the invention with molten cobalt nitrate, whether or not hydrated but other cobalt molten salts that meet the criteria of melting before decomposing may be used, for example, $CoBr_2.6H_2O$ (Tm=47° C.), $CoCl_2.6H_2O$ (Tm86° C.), $Co(C_{16}H_{31}O_2)_2$ (palmitate, Tm=70.5° C.), $Co(OOCC_6H_5)_2$ (benzoate, Tm=115° C.), $Co(C_5H_7O_2)_3$ (pentanedionate, Tm=216° C.), etc.

While not wishing to be bound by an particular theory, the use of the substantially anhydrous molten salt for impregnation may create a situation where the active species, e.g., the cobalt nitrate molten salt, is strongly adsorbed by the support particle and diffusion of this active species is limited. The presence of water reduces the adsorptivity of the active species while decreasing solution viscosity and allows capillary inhibition to be the predominant transport process, thereby creating a particle throughout which the cobalt is evenly distributed. However, if capillary forces are small compared to the inertial (viscous) forces, the particle will have the cobalt concentrated on its exterior surface with very little, if any, cobalt on the interior surface. The use of additives to change capillary transport characteristics and limiting the time of contact are well known procedures for concentrating a catalytic metal at any portion or portions of the catalyst particle. (Reference: S. Kulkarni et al, J. Catal. 69, 445 (1981), and references therein.

Where the production of a rim type catalyst is not desired, it is not necessary to use molten salt starting materials. This is because viscosity is not of critical importance when making non-rim catalyst; therefore, solution salts containing a suitable solvent may be used.

Suitable solvents include, for example, water, ketones, such as acetone, butanone (methyl ethyl ketone); the lower alcohols, e.g., methanol, ethanol, propanol and the like; amides, such as dimethyl formamide; amines, such as butylamine; ethers, such as diethylether and tetrahydrofuran; and mixtures of the foregoing solvents. Preferred solvents are acetone and aqueous acetone.

After depositing the cobalt onto the support, such as, silica, the catalytic precursor is dried, for example, at about 120° C. for about 30 minutes to several hours. The reduction follows the drying step directly so that a separate high temperature calcination step (wherein the catalyst is heated above about 250°-500° C. in an oxygen containing stream to convert the catalytic metal salt to the oxide) is omitted. The reduction takes place in the presence of a reducing agent, preferably hydrogen gas, at a steady heating rate of less than about 1° C./min. and preferably less than about 0.4° C./min. and more preferably less than about 0.2° C./min. to a maximum temperature ranging from about 200°-500° C. for a period of time sufficient to substantially reduce the valence state of the cobalt to zero.

The phrase "steady heating rate" as used herein, is defined as a rate where the ratio of temperature change in degrees centigrade (°C.) as a function of time (°C./min.) is constant.

The phrase "drying" or "dried" as used herein is defined as a procedure wherein the raw catalyst sample is heated to substantially remove liquid phase components, such as water or other solvents, from the catalyst particle. This is generally achieved by heating the catalyst to temperatures up to 120° C. for from 30 minutes to several hours.

Table A, below, shows the effect of high temperature calcination on a cobalt/silica catalyst and on site density. As can be seen, greater site density is achieved in the absence of the usual calcination step. During high temperature calcination, generally conducted at temperatures in excess of about 200° C., e.g, 300° to 400° C., cobalt tends to agglomerate, as the oxide, into larger particles which remain after the subsequent reduction step and result in lower dispersion. As noted above, by eliminating the high temperature calcination step and directly reducing the catalyst to the metal, agglomeration is avoided and dispersion is enhanced.

TABLE A

EFFECT OF CALCINATION ON COBALT DISPERSION
($Co/SiO_2$, Catalyst B)

| Pretreatment | Site Density g-atom Co surface liter catalyst | Dispersion (%) |
|---|---|---|
| Calcination/450° C. Reduction/450° C. | 0.032 | 2.9 |
| Direct Reduction/450° C. | 0.064 | 5.7 |

We have also found that slower single steady heating rates during the reduction step of less than about 1° C./min. avoid catalyst metal sintering and produce a catalyst having increased dispersion. One possible theory is that the slower heating rate causes a decreased evolution rate of cobalt salt solution reduction products, such as, $NO_2$, $H_2O$, NOx, and potential decomposition products of the anion of the salt (e.g., HBr, HOAc, etc. for nitrate free salts). This in turn is believed to cause dissolution and sintering of the cobalt particles.

In addition, the relatively slow heating rate allows ample time at lower temperatures for the precursor salt to decompose. This precludes the need to expose the catalyst to excessively high temperatures which would lead to thermal sintering, i.e., the growth of large, relatively low surface area cobalt crystallites. The method of this invention allows the synthesis of highly dispersed cobalt, and reduces the need for other structural or electronic promoters such as thoria, ruthenium and platinum, which in the prior art are taught to increase catalyst activity.

Preparation of catalysts in accordance with this invention leads to catalysts of enhanced dispersion, wherein the cobalt particles are smaller than expected, i.e., below about 170 angstroms, and more of the cobalt atoms are available to catalyze the desired reaction between carbon monoxide and hydrogen to form heavy hydrocarbons such as $C_5+$. As the cobalt site density is increased, the use of the rim catalyst in hydrocarbon synthesis reactions also increases the $C_5+$ productivity (defined as the volume of CO converted to $C_5+$ per volume of catalyst per hour).

The invention will be further illustrated by the following examples. The examples are not to be taken as limiting the scope of the invention in any way.

EXPERIMENTAL PROCEDURES

A. Chemisorption

Physisorption and chemisorption techniques in the characterization of supported catalysts was first demonstrated in the elegant work of Emmett, P.H., Brunauer, S., J. Am. Chem. Soc., 56, 35 (1934). Measurements of total surface area using dinitrogen physisorption (BET) were followed by the use of selective dinitrogen chemisorption to determine the number of Fe surface atoms on promoted ammonia synthesis catalysts.

We have used molecular hydrogen as a probe of surface cobalt atoms in hydrocarbon synthesis catalysts. We measured dihydrogen uptakes in an all-glass static chemisorption unit, pumped by diffusion and roughing pumps isolated from the system by liquid nitrogen traps, and capable of a dynamic vacuum of $10^{-7}$ Torr. Prereduced and passivated samples were rereduced in flowing dihydrogen (200 $cm^3$(STP)/g-cat-min) for 1–2 hours at 200°–800° C., and then evacuated to less than $10^{-6}$ Torr for 0.5–1 hour at a temperature sufficient to remove all chemisorbed hydrogen (>250° C.). The samples were then cooled to the adsorption temperature ($-77°$ to 150° C.) and isotherms were measured at 3 to 5 hydrogen pressures between 100 and 700 Torr. A backsorption isotherm was sometimes measured by evacuating the sample to 10-6 Torr at the adsorption temperature for 0.5 h, and then measuring the hydrogen uptakes again between 100 and 500 Torr. Adsorption and backsorption isotherms were extrapolated to zero pressure to obtain the total and weak chemisorption uptakes, respectively.

Dispersions were calculated from the total hydrogen uptakes at 100° C. and from the cobalt content of the samples, assuming a 1:1 stoichiometry of hydrogen to surface cobalt atoms. Dispersion is defined as the fraction or percentage of the total number of cobalt atoms in the catalyst that reside at the surface of cobalt crystallites and provides a convenient measure of the number of surface sites that are available for catalysis.

B. Cobalt Distributions

Cobalt distributions within support pellets were obtained by x-ray line profiles using a JEOL-35C in the SEM mode, with an annular, backscattered electron detector, a four crystal X-ray wavelength spectrometer, and a PGT System 4 x-ray energy dispersive spectrophometer. Wavelength dispersive scans collect element-specific Co K-$\alpha$ radiation, at an accelerating voltage of 25 Kev.

C. Support Surface Area/Pore Volume Distributions

Support surface areas and pore volume distributions were measured by dinitrogen physisorption at 77K, as described in Smith, J.M., Chemical Engineering Kinetics, McGraw-Hill, pp. 291-318, 2nd Edition, 1970.

EXAMPLE 1

Preparation of 13% $Co/SiO_2$ Rim Catalyst (Catalyst B) by Melt-Impregnation Technique Silica spheres of nominal 2.2 mm diameter are calcined for 16 hours at 600° C. Surface area measures 80 $m^2$/g with a pore volume of 1.0 ml/g. 12.5 grams of the spheres are weighed out. 50 grams of $Co(NO_3)_2.6H_2O$ are weighed out into a flask and heated to melt the cobalt nitrate salt. Temperature is kept between 85° and 95° C. No additional water or other solvent is added to the melt. The silica spheres are added to a vacuum filter that contains a 5 to 10 mm layer of 6 mm hollow glass beads. The molten cobalt nitrate solution is poured over the silica spheres with vacuum applied so that the residence time of the molten liquid is approximately 2-4 sec. The spheres are then dried at 120° C. Measurement of the penetration depth of the cobalt is 0.05-0.15 mm (FIG. 1). The cobalt loading is 13%. This indicates that the local loading in the rim is 40 to 50%. The sample is reduced at 0.2 deg. C./min. from room temperature to 350 deg. C. The dispersion of cobalt is 5.5% corresponding to 170Å diameter crystallites assuming hemispherical particles.

A comparative sample is prepared by dissolving the 50 grams of cobalt nitrate in 75 cc of water. This solution is added to 12.5 grams of the silica spheres in a vacuum funnel with a layer of porous glass beads. The sample is dried at 120° C. Cobalt now has penetrated into the entire sphere. The cobalt distribution is very similar to that of Catalyst A (see Example 3).

EXAMPLE 2

Preparation of 20.9% Co/SiO$_2$ Rim Catalyst (Catalyst E) by Melt-Impregnation Technique Silica spheres of nominal 2.2 diameter are calcined for 16 hours at 600° C. Surface area measures 350 m$^2$/g with a pore volume of 1.3 ml/g. 12.5 grams of the spheres are weighed out. 50 grams of Co(NO$_3$)$_2$.6H$_2$O are placed in a flask and heated to melt the cobalt nitrate salt. Temperature is kept at between 75° and 85° C. No additional water or other solvent is added to the melt. The silica spheres are added to a vacuum filter that contains a 5 to 10 mm layer of 6 mm hollow glass beads. The molten cobalt nitrate solution is poured over the silica spheres with vacuum applied so that the residence time of the molten liquid is approximately 2-4 sec. The spheres are then dried at 120° C. The sample is reduced at 0.2 deg. C./min from room temperature at 350 deg. C. Melt impregnation and reduction procedures are repeated on prereduced sample. Cobalt dispersion is 7.3% corresponding to 130Å diameter crystallites. The higher surface area support leads to better Co dispersion than in Catalyst B, in spite of the much higher cobalt loading in this catalyst.

EXAMPLE 3

Preparation of Evenly Impregnated 13% Co/SiO$_2$ Spheres (Catalyst A)

Co(NO$_3$)$_2$.6H$_2$O (17.4g) was dissolved in enough water to make a solution of 30 cc total volume. This solution was contacted (incipient wetness) with 20 grams of the silica spheres used in Catalyst B. The spheres were dried at 120° C. Examination indicated that the cobalt had penetrated into the entire sphere. The, cobalt loading is 13% wt. (Catalyst A).

EXAMPLE 4

Preparation of 13% Co/SiO$_2$ Powder by Grinding of Catalyst B (Catalyst C)

Catalyst B is ground and passed through 80/140 mesh screens to isolate catalysts particles sized between 100 and 150 microns.

EXAMPLE 5

Preparation of 14.5% Co/SiO$_2$ Powder by Incipient Wetness of Powder with Cobalt Nitrate Solution (Catalyst D)

SiO$_2$ Powder (Davison 62, 100-180 um pellet size, 280 m$^2$g$^{-1}$) was impregnated to incipient wetness with cobalt nitrate solution to give a uniform cobalt loading of 14.5% wt. The catalyst was dried overnight at 120° C., and reduced in flowing hydrogen at 450° C.

EXAMPLE 6

Preparation of 11% Co/0.6% Zr/SiO$_2$ Catalyst as Described in U.S. Pat. No. 4,599,481 (Catalyst F)

This preparation was carried out following the procedure for catalyst 4 outlined in the patent, 138 g of Co(NO$_3$)$_2$.6H$_2$O was dissolved in 200 cc of 99.9% ethanol (15 wt % Co). 15 g of silica spheres 350 m$^2$/g, 2.2 mm diameter were immersed in the above solution at room temperature for 5 seconds. The spheres were then dried for 2 hours at 100° C. and then calcined at 500° C. for 1 hour. The immersion/dry/calcine sequence was repeated one more time to complete the cobalt loading step, as described in the aforementioned patent.

The zirconium was loaded using incipient wetness. 1 wt % Zr was prepared by dissolving 0.25 g of ZrO(NO$_3$)$_2$xH$_2$O (H$_2$O=3%) in 13 cc H$_2$O. This solution was added dropwise of 10 g of the above silica spheres. The solution was dried at 100° C. for 2 hours and calcined at 500°C. for 1 hour. The sample was then reduced at 250°C. for 24 hours with an 0.2° C./min heat-up rate in flowing hydrogen.

EXAMPLE 7

Comparison of Evenly Distributed Catalyst (Catalyst A) and Rim Catalyst (Catalyst B); Cobalt on 2.2 mm SiO$_2$ Spheres The hydrocarbon synthesis activity and selectivity of evenly impregnated (A) and radially impregnated (B) Co on 2.2 mm SiO$_2$ spheres were measured in a fixed bed plug flow reactor at 200° C., 2,100 KPa, H$_2$/CO=2, at a space velocity required for 60-65% CO conversion. All reported data were obtained after at least 75 h on stream.

Placing the active Co sites within 100-150 microns of the SiO$_2$ sphere surface increased the volumetric activity from 90 to 150 h$^{-1}$, in spite of a higher local loading (40 vs 13%) and a concomitant lower dispersion 5.5 vs 6.3% in the rim catalyst. (Table 1) Also CH$_4$ selectivity decreases (12.0 to 8.3%) and C$_5$+ selectivity increases (82 to 87%) when cobalt is non-uniformly impregnated.

The activity and selectivity on the rim cobalt catalyst resemble those on an evenly impregnated 150 um Co/SiO$_2$ powder (Table 1). CH$_4$ selectivity is slightly higher in the rim catalyst (8.3 vs 7.5%) but because of a much lower C$_2$-C$_4$ selectivity (4.4 vs 9.2%), C$_5$+ selectivity is actually higher in the rim catalyst (87 vs 83%).

The results suggest that diffusional limitations are almost completely eliminated by concentrating cobalt in the outer surface and that the volumetric activity and selectivity of conventional powders can be achieved with commercial-sized pellets, by using radially impregnated (or rim) catalysts prepared by the method of this invention.

EXAMPLE 8

Crushing of Co/SiO$_2$ Rim

An additional activity and $C_5+$ selectivity increase was obtained when the rim catalyst was crushed into smaller particles, suggesting slight diffusional limitations were still operative in 100–150 um rims (Catalyst B). Volumetric rates increased from 150 to 210 h$^{-1}$ and $C_5+$ selectivity from 87 to 90.5 %. CH$_4$ selectivity decreased from 8.3 to 4.7% but $C_2$-$C_4$ selectivity was not affected.

TABLE 1

Comparison of Even and Rim Co on SiO$_2$ Spheres (13% wt. Co)

| | Catalyst A Even (2.2 mm Spheres) | Catalyst B Rim (100–150 um on 2.2 mm spheres) | Catalyst D 13% Co/SiO$_2$ (100–150 um powder) |
|---|---|---|---|
| Site Density (g-atom surface Co/liter cat) | 0.069 | 0.064 | 0.065 |
| Space Velocity (CM$^3$ H$_2$ + CO/Cm$^3$ cat · h) | 420 | 650 | 920 |
| CO Conversion (%) | 64.5 | 66.0 | 48.0 |
| Volumetric Rate (cm$^3$ CO converted/cm$^3$ cat · h) | 90 | 150 | 150 |
| Selectivity (%) | | | |
| CH$_4$ | 12.0 | 8.3 | 7.5 |
| C$_2$-C$_4$ | 5.1 | 4.4 | 9.2 |
| C$_5+$ | 82.0 | 87.0 | 83.2 |
| CO$_2$ | 0.9 | 0.4 | 0.2 |
| Cobalt-Time Yield (mole CO/g-atom CO surface · h) | 3.3 | 5.7 | 5.3 |
| Cobalt dispersion (mole Co/g-atom CO surface · h) | 6.3 | 5.5 | 6.0 |
| Site-Time-Yield (mole-CO/g-atom Co surface · h) | 50 | 100 | 90 |
| Run | 135–149 | 134–268 | 128–827 |
| Time on stream (/h) | 193 | 318 | 76 |
| Conditions: 200° C., 2100 kPa, H$_2$/CO = 2 | | | |

TABLE 2

Comparison of Crushed and Uncrushed Rim Co on SiO$_2$ (13% wt. Co)

| | Catalyst B Rim (2.2 mm SiO$_2$ Spheres) | Crushed Catalyst B (0.1–0.2 mm granules) |
|---|---|---|
| Site Density (g-atom surface Co/liter cat) | 0.064 | 0.064 |
| Space Velocity (CM$^3$ H$_2$ + CO/Cm$^3$ cat · h) | 650 | 940 |
| CO Conversion (%) | 66.0 | 48.0 |
| Volumetric Rate (cm$^3$ CO converted/cm$^3$ cat · h) | 150 | 210 |
| Selectivity (%) | | |
| CH$_4$ | 8.3 | 4.7 |
| C$_2$-C$_4$ | 4.4 | 4.7 |
| C$_5+$ | 87.0 | 90.5 |
| CO$_2$ | 0.4 | 0.1 |
| Cobalt-Time Yield (mole CO/g-atom CO surface · h) | 5.7 | 5.5 |
| Cobalt dispersion (mole Co/g-atom CO surface · h) | 5.5 | 5.5 |
| Site-Time-Yield (mole-CO/g-atom Co surface · h) | 100 | 150 |
| Run | 134–268 | 137–538 |
| Time on stream (/h) | 318 | 175 |
| Conditions: 200° C., 2100 kPa, H$_2$/CO = 2 | | |

EXAMPLE 9

Comparison of High Loading/High Surface Area (Catalyst E) and Low Loading/Low Surface Area (Catalyst B) Rim Catalysts Prepared by Melt Impregnation Increasing support surface area from 80 to 350 m$^2$g$^{-1}$ allowed the use sequential melt impregnation procedures to give higher cobalt loading (20.9 vs 13 wt. %) with an actual increase in cobalt dispersion. As a result, volumetric rates increased from 150 to 342 h$^{-1}$ at 2,100 kPa, 200° C., and 2.1 H$_2$/CO ratio (Table 3). A the same conditions, $C_5+$ productivity increased from 130 to 278 h$^{-1}$. The required catalyst volume for a given productivity per reactor can be decreased by a factor of two. $C_5+$ selectivity decreases slightly because of increased CO diffusional limitations for the higher activity 20.9% Co/SiO$_2$ catalyst, but it is more than compensated by the higher total volumetric productivity of Catalyst E.

TABLE 3

Comparison of High Surface Area/High Loading and Low Surface Area/Low Loading Co/SiO$_2$ Rims (200° C.)

| | | |
|---|---|---|
| Site Density (g-atom surface Co/liter cat) | 0.064 | 0.129 |
| Rim Thickness (u) | 80 ± 30 | 120 ± 30 |
| Catalyst | B | E |
| (support area/m$^2$ g$^{-1}$) | 80 | 350 |
| % Co Loading | 13 | 20.9 |
| Space Velocity (cm$^3$ H$_2$ + CO/Cm$^3$ cat · h) | 650 | 1750 |
| CO Conversion (%) | 66 | 64 |
| Volumetric Rate (cm$^3$ CO converted/cm$^3$ cat · h) | 150 | 342 |
| Selectivity (%) | | |
| CH$_4$ | 8.3 | 12.7 |
| C$_2$-C$_4$ | 4.4 | 5.3 |
| C$_5+$ | 87.0 | 81.3 |
| CO$_2$ | 0.4 | 0.7 |
| C$_2+$ productivity (cc CO to C$_2+$/cc cat · h) | 137 | 296 |
| C$_5+$ productivity (cc CO to C$_5+$/cc cat · h) | 130 | 278 |
| Cobalt-Time Yield (mole CO/g-atom CO · h) | 5.7 | 9.5 |
| Cobalt Dispersion (surface Co/total Co × 100%) | 5.5 | 7.3 |
| Site-Time-Yield (mole-CO/g-atom Co surface · h) | 100 | 130 |
| Run | 134–268 | 154–657 |
| Time on stream (/h) | 318 | 315 |
| Pressure (/kPa) | 2100 | 2100 |
| H$_2$/CO ratio | 2.1 | 2.1 |

EXAMPLE 10

Comparison of 20.9% Co/SiO₂ Rim (Catalyst E) at 2.1 and 1.65 H₂/CO Ratios $CH_4$ selectivity can be decreased, and $C_5+$ selectivity increased, with little change in total volumetric productivity by operating the catalyst at a sub-stoichiometric $H_2/CO$ ratio (1.65 to 2.1) (Table 4). $CH_4$ selectivity decreases markedly from 12.7 to 7.7%, while $C_5+$ selectivity increases from 81.3 to 85.9%. $C_5+$ productivity decreases by about 10%, from 278 $h^{-1}$ to 241 $h^{-1}$. This mode of operation allows more effective utilization of the synthesis gas, while maintaining the high volumetric productivity observed at the stoichiometric consumption ratio (2.1/1) on these Co/SiO₂ rim catalysts.

TABLE 4

| Effect of Decreasing H₂/CO Ratio From 2.10 to 1.65 (20.9% Co/SiO₂ Rim) | | |
| --- | --- | --- |
| Space Velocity (cm³ H₂ + CO/cm³ cat · h) | 1750 | 1250 |
| CO Conversion (%) | 64 | 62.5 |
| Volumetric Rate (cm³ CO converted/cm³ cat · h) | 342 | 280 |
| Selectivity (%) | | |
| CH₄ | 12.7 | 7.7 |
| C₂-C₄ | 5.3 | 5.6 |
| C₅+ | 81.3 | 85.9 |
| CO₂ | 0.70 | 0.80 |
| C₂+ productivity (cc CO to C₂+/cc cat · h) | 296 | 258 |
| C₅+ productivity (cc CO to C₅+/cc cat · h) | 278 | 241 |
| Cobalt-Time Yield (mole CO/g-atom CO · h) | 9.5 | 7.7 |
| Cobalt Dispersion (surface Co/total Co × 100%) | 7.3 | 7.3 |
| Site-Time-Yield (mole-CO/g-atom Co surface · h) | 130 | 107 |
| Run | 154-657 | 154-681 |
| Time on stream (/h) | 315 | 385 |
| Pressure (/kPa) | 2100 | 2100 |
| H₂/CO ratio | 2.1 | 1.65 |

EXAMPLE 11

Comparison of 20.9% Co/SiO₂ Rim (Catalyst E) at 630 and 2,100 kPa (Ho/CO-2.1)

Methane Selectivity can be decreased, and $C_5+$ selectivity and productivity increased by operating the catalyst at elevated pressure. Increasing $H_2/CO$ pressure from 630 to 2,100 kPa at 2.1/1 $H_2/CO$ ratio decreases methane selectivity from 20.6 to 13.5%, while $C_5+$ selectivity and productivity increase from 67 to 80.9% and 94.5% to 302 $h^{-1}$, respectively (Table 5). This elevated pressure mode of operation not only decreases catalyst volume for a given reactor productivity, but also allows more efficient utilization of the synthesis gas feed, by minimizing the fraction of it converted to undesired products.

TABLE 5

| Pressure Effect on 20.9% Co/SiO₂ Rim (Catalyst E) (H₂O/CO - 2.1) | | |
| --- | --- | --- |
| Space Velocity (cm³ H₂ + CO/cm³ cat · h) | 750 | 1915 |
| CO Conversion (%) | 61 | 63.5 |
| Volumetric Rate (cm³ CO converted/cm³ cat · h) | 141 | 373 |
| Selectivity (%) | | |
| CH₄ | 20.6 | 13.5 |
| C₂-C₄ | 10.8 | 5.1 |
| C₅+ | 67.0 | 80.9 |
| CO₂ | 1.6 | 0.5 |
| C₂+ productivity (cc CO to C₂+/cc cat · h) | 110 | 321 |
| C₅+ productivity (cc CO to C₅+/cc cat · h) | 94.5 | 302 |
| Cobalt-Time Yield (mole CO/g-atom CO · h) | 3.9 | 10.3 |
| Cobalt Dispersion (surface Co/total Co × 100%) | 7.3 | 7.3 |
| Site-Time-Yield (mole-CO/g-atom Co surface · h) | 50 | 140 |
| Run | 154-628 | 154-635 |
| Time on stream (/h) | 145 | 170 |
| Pressure (/kPa) | 630 | 2100 |
| H₂/CO ratio | 2.1 | 2.1 |

EXAMPLE 12

Comparison of 20.9% Co/SiO₂ Rim (Catalyst E) at 2,100 and 4,000 kPa (H₂/CO-1.65)

Methane Selectivity can be decreased, and $C_5+$ productivity increased by operating the catalyst at elevated pressure. Increasing $H_2/CO$ pressure from 2,100 to 4,000 kPa at a 1.65 $H_2/CO$ ratio decreases methane selectivity from 7.5 to 7.2%, while $C_5+$ productivity increases from 221 to 264 $h^{-1}$, (Table 6). This elevated pressure mode of operation not only decreases catalyst volume for a given reactor productivity, but also allow more efficient utilization of the synthesis gas feed, by minimizing the fraction of it converted to undesired products.

TABLE 6

| Effect of Increasing Pressure from 200 kPa to 4000 kPa (H₂/CO - 1.65, Catalyst E) 20.9 Co/SiO₂ Rim Catalyst | | |
| --- | --- | --- |
| Space Velocity (cm³ H₂ + CO/cm³ cat · h) | 1170 | 1500 |
| CO Conversion (%) | 61.5 | 58 |
| Volumetric Rate (cm³ CO converted/cm³ cat · h) | 255 | 310 |
| Selectivity (%) | | |
| CH₄ | 7.5 | 7.2 |
| C₂-C₄ | 4.9 | 6.9 |
| C₅+ | 86.7 | 85.2 |
| CO₂ | 0.85 | 0.80 |
| C₂+ productivity (cc CO to C₂+/cc cat · h) | 234 | 285 |
| C₅+ productivity (cc CO to C₅+/cc cat · h) | 221 | 264 |
| Cobalt-Time Yield (mole CO/g-atom CO · h) | 7.07 | 8.50 |
| Cobalt Dispersion (surface Co/total Co × 100%) | 7.3 | 7.3 |
| Site-Time-Yield (mole-CO/g-atom Co surface · h) | 98 | 118 |
| Run | 154-688 | 154-720 |
| Time on stream (/h) | 508 | 530 |
| Pressure (/kPa) | 2100 | 4000 |
| H₂/CO ratio | 1.65 | 1.65 |

EXAMPLE 13

Comparison of Rim Catalyst from U.S. Pat. No. 4,599,481 (Co/Zr/SiO₂, Catalyst F) With Melt Impregnated Catalysts of This Invention (Catalyst B and E)

Catalysts B and E show 2.0 to 4.6 times the $C^2+$ productivity of Catalyst F (Table 7). Total volumetric rates are 2.1 to 4.9 times higher on the catalysts of this invention. These improvements are the result of the thinner Co-coated region and of the sharper cobalt profiles obtained with the melt impregnation technique. The absence of Zr, and our pretreatment conditions (no calcination/slow reduction) also lead to a larger fraction of the loaded cobalt being available to reactants during catalysis (higher cobalt dispersion). Finally, when compared at equal $CH_4$ and $C_2+$ selectivities, rather than at constant $H_2/CO$ ratio, Catalyst E still give 4.3 times higher $C_2$ productivity than Catalyst F (Table 8).

TABLE 7

Comparison of Rim Catalyst (F, Co/Zr/SiO$_2$) with 13% Co/SiO$_2$ (Catalyst B) with 20.9% Co/SiO$_2$ Rim Catalyst (E) (at Identical Operating Conditions, 200° C.)

| Catalyst | F | B | E |
|---|---|---|---|
| Site Density (g-atom surface Co/liter cat) | 0.033 | 0.064 | 0.129 |
| Space Velocity (CM$^3$ H$_2$ + CO/Cm$^3$ cat · h) | 380 | 650 | 1750 |
| CO Conversion (%) | 60 | 66 | 64 |
| Volumetric Rate (cm$^3$ CO converted/cm$^3$ cat · h) | 70 | 150 | 342 |
| Selectivity (%) | | | |
| CH$_4$ | 7.3 | 8.3 | 12.7 |
| C$_2$-C$_4$ | — | 4.4 | 5.3 |
| C$_5$+ | — | 87.0 | 81.3 |
| CO$_2$ | 0.4 | 0.40 | 0.70 |
| C$_5$+ productivity (cc Co to C$_5$+/CC cat · h) | — | 137 | 278 |
| C$_2$+ productivity (cc Co/ to C$_2$+/cc cat · h) | 65 | 130 | 296 |
| Cobalt-Time Yield (mole CO/g-atom Co surface · h) | 4.0 | 5.7 | 9.5 |
| Cobalt dispersion (mole Co/g-atom Co surface · h) | 3.5 | 5.5 | 7.3 |
| Site-Time-Yield (mole-CO/g-atom Co surface · h) | 115 | 100 | 130 |
| Run | 200-6 | 134-268 | 154-657 |
| Time on stream (/h) | 216 | 318 | 315 |
| Pressure (/kPa) | 2100 | 2100 | 2100 |
| H$_2$/CO | 2.1 | 2.1 | 2.1 |

TABLE 8

Comparison of Rim Catalyst (F, H$_2$/CO - 2.1) and Melt-Impregnated 20.9% Co/SiO$_2$ (E, H$_2$/CO - 1.65), 200° C. at Equal C$_2$+ Selectivities

| Catalyst | E | F |
|---|---|---|
| Site Density (g-atom surface Co/liter cat) | 0.129 | 0.033 |
| Space Velocity (CM$^3$ H$_2$ + CO/Cm$^3$ cat · h) | 1250 | 380 |
| CO Conversion (%) | 62.5 | 60 |
| Volumetric Rate (cm$^3$ CO converted/cm$^3$ cat · h) | 300 | 70 |
| Selectivity (%) | | |
| CH$_4$ | 7.7 | 7.3 |
| C$_2$-C$_4$ | 5.6 | — |
| C$_5$+ | 85.9 | — |
| CO$_2$ | 0.80 | 0.4 |
| C$_2$+ productivity (cc Co/ to C$_2$+/cc cat · h) | 275 | 65 |
| C$_5$+ productivity (cc Co to C$_5$+/CC cat · h) | 260 | — |
| Cobalt-Time Yield (mole CO/g-atom CO surface · h) | 7.7 | 4.0 |
| Cobalt dispersion (mole Co/g-atom Co surface · h) | 7.3 | 3.5 |
| Site-Time-Yield (mole-CO/g-atom Co surface · h) | 107 | 115 |
| Run | 154-676 | 200-6 |
| Time on stream (/h) | 345 | 216 |
| Pressure (/kPa) | 2100 | 2100 |
| H$_2$/CO | 1.65 | 2.1 |

EXAMPLE 14

A Variation on the Method for Preparing Rim Type Cobalt on Silica Catalysts (Catalyst G)

The preparation is a vacuum-assisted molten cobalt nitrate (Co/NO$_3$)$_2$.6H$_2$O) loading method. Silica spheres were placed in a filter funnel with a vacuum flask underneath. The molten cobalt nitrate was poured over and filtered through the evacuating silica sphere bed. Specifically, using a 1.5 inch diameter glass filter funnel with a 12 mesh 304 SS screen inserted in the bottom. A charge of 12.5 grams of silica spheres (1.5 mm diameter) was placed in the filter funnel creating a 1 inch bed height. The filter funnel is placed on top of a filter flask and a vacuum was pulled on the bed. 30 grams of cobalt nitrate (ACS Grade) were placed in a beaker on a hot plate and heated to 80 degrees centigrade. The cobalt nitrate liquid was removed from the hot plate and allowed to cool to 70 degrees centigrade. The molten cobalt nitrate was quickly poured over the evacuating silica spheres and the excess liquid was pulled through the bed and into the vacuum flask. The silica spheres were immediately stirred with a glass stirring rod to minimize sticking and poured out into a porcelain bowl. The cobalt nitrate coated spheres were oven dried at 100 degrees centigrade for two hours and then reduced in flowing hydrogen at 320 degrees centigrade. The entire procedure was repeated to increase the cobalt loading to 27% wt.

This method results in a catalyst of well defined metal penetration, and high site density. Table 9 shows that this preparation procedure leads to a catalyst of high activity and site density, having with decreased CH$_4$ selectivity (5.1 vs. 7.7%) and increased C$_5$+ selectivity (90.1 vs 85.9%).

TABLE 9

Comparison of Catalyst E (Example 2) and G (Example 14)

| Catalyst | G | E |
|---|---|---|
| Space Velocity (CM$^3$ H$_2$ + CO/Cm$^3$ cat · h) | 1100 | 1250 |
| CO Conversion (%) | 64 | 62.5 |
| Volumetric Rate (cm$^3$ CO converted/cm$^3$ cat · h) | 250 | 280 |
| Selectivity (%) | | |
| CH$_4$ | 5.1 | 7.7 |
| C$_2$-C$_4$ | 3.9 | 5.6 |
| C$_5$+ | 90.1 | 85.9 |
| CO$_2$ | 0.9 | 0.80 |
| C$_2$+ productivity (cc Co/ to C$_2$+/cc cat · h) | 235 | 258 |
| C$_5$+ productivity (cc Co to C$_5$+/CC cat · h) | 226 | 241 |
| Cobalt-Time Yield | 4.9 | 7.7 |

TABLE 9-continued

Comparison of Catalyst E (Example 2) and G (Example 14)

| Catalyst | G | E |
|---|---|---|
| (mole CO/g-atom CO · h) | | |
| Cobalt dispersion | 5.8 | 7.3 |
| (surface Co/total Co × 100%) | | |
| Site-Time-Yield | 88 | 107 |
| (mole-CO/g-atom | | |
| Co surface · h) | | |
| Run | 51/848–842 | 154–681 |
| Time on stream (/h) | 220 | 385 |
| Pressure (/kPa) | 2100 | 2100 |
| $H_2$/CO | 1.65 | 1.65 |
| Site Density | 0.126 | 0.129 |
| (g-atom surface Co/ | | |
| liter cat) | | |
| % Co | 27.0 | 20.9 |

EXAMPLE 15

Preparation of 10% Co/$SiO_2$ Powder Catalyst by Incipient Wetness Technique and Steady Heating Rates A cobalt solution, containing an equal volume cobalt solution to the pore volume of the support was prepared by dissolving 14.85 g of the hexahydrate of cobalt nitrate in acetone so that the total volume of solution equaled 54 cc. The solution was added dropwise to 27 g of precalcined Davison 62 silica to impregnate by incipient wetness the cobalt on the silica support. For incipient wetness impregnation to occur, 2 cc of acetone per gram of silica was required. The resulting catalyst was dried at 120° C. and reduced during various runs of different steady heating rates in the presence of $H_2$ to the temperature indicated. In some cases, the catalyst was subjected to the sequence of pretreatment steps as shown in Table 10. The results show improved dispersion for the slower single steady heating rates. The data also confirms that high dispersion, ergo enhanced catalyst activity, can be achieved by direct reduction of the catalyst from the impregnated cobalt nitrate support, rather than by first cooling the precursor. Most preferably, a combination of slow heating rate of the impregnated cobalt nitrate support (with no oxidation step) and a high gas space velocity produces the highest dispersion and most active catalysts. The data also shows that once formed by the initial reduction, subsequent oxidation/reduction cycles do not markedly affect the dispersion.

TABLE 10

| Run | Pre-treatment Sequence | Heating Rate and Reduction Temp. (°C./Min.) | Reduction Temp. (°C.) | Temp. Chemisorption (°C.) | Percent Dispersion |
|---|---|---|---|---|---|
| A | $H_2$ | 0.1 | 300 | 300 | 8.6 |
| | | | | 400 | 9.1 |
| | | | | 500 | 8.2 |
| | | | | 600 | 7.3 |
| B | $H_2/O_2/H_2$ | 0.1 | 300 | 250 | 7.4 |
| | | | | 350 | 8.5 |
| | | | | 500 | 7.7 |
| C | $H_2$ | 0.1 | 300 | 350 | 8.8 |
| | | | | 450 | 10.2 |
| D | $H_2$ | 4.0 | 500 | 450 | 5.2 |
| E | $O_2/H_2$ | 4.0 | 500 | 350 | 3.5 |
| F | $H_2/O_2/H_2$ | 4.0 | 500 | 300 | 6.8 |
| | | | | 500 | 5.6 |
| G | $H_2$ | 0.2 | 350 | 350 | 5.5 |

Notes:
Runs A through F - Involved powdered catalysts prepared by incipient wetness impregnation.
Run C - The normal gas space velocity SHSV of 3500 cc/g cat/hr. was increased to 5300 cc/g cat/hr.
Run G - The catalyst was a rim type catalyst prepared by a melt impregnation technique (see Example 1).

We claim:

1. A method for preparing a supported cobalt catalyst particle which comprises:
   (a) contacting a support particle with a molten cobalt salt, for a period sufficient to impregnate substantially all of the molten cobalt salt on the support to a depth of less than about 200 um;
   (b) drying the supported cobalt salt obtained in step (a) and;
   (c) reducing the cobalt of the supported cobalt salt in step (b) to metallic cobalt by heating the salt in the presence of $H_2$, wherein the heating is conducted at a rate of less than about 1° C./min. up to a maximum temperature ranging from about 200° C. to about 500° C., to produce a supported cobalt catalyst particle.

2. The method of claim 1 wherein the heating is conducted at a rate of less than about 0.4° C./min.

3. The method of claim 1 wherein the molten salt is at a temperature between its melting point and its decomposition temperature and wherein the contacting occurs in the substantial absence of water other than the water of hydration.

4. The method of claim 3 wherein the molten salt is cobalt nitrate or hydrated cobalt nitrate.

5. The method of claim 3 wherein the period sufficient to deposit the metal salt on the support is less than about 10 seconds.

6. The method of claim 1 wherein the support is selected from the group consisting of silica, magnesia, alumina, silica-alumina, titania, and mixtures thereof.

7. A method of preparing a supported cobalt rim-type catalyst particle which comprises:
   (a) contacting an inorganic refractory oxide support particle with a molten cobalt salt, in the substantial absence of water other than the water of hydration, at sufficient viscosity and loading conditions to prevent capillary action within the support material from allowing the transport of said cobalt salt into the interior regions of the support, for a period of time sufficient to deposit at least 95 wt. % of the cobalt in a rim of less than about 200 um in thickness from the external surface of the particle,
   (b) drying the particle and;
   (c) reducing the particle to metallic cobalt by heating the particle in the presence of $H_2$, wherein the heating is conducted at a rate of less than about 1° C./min. to a maximum temperature ranging from about 200° C. to about 500° C. and wherein the molten cobalt salt is at a temperature between its melting point and its decomposition temperature to produce a supported cobalt rim type catalyst particle.

8. The method of claim 7 wherein the heating is conducted at a rate of about 0.2° C./min.

9. The method of claim 7 wherein the molten cobalt salt is cobalt nitrate or hydrated cobalt nitrate.

10. The method of claim 7 wherein the resulting catalyst has a cobalt dispersion of greater than about 4% and the cobalt site density is at least about 0.05 g-atom surface Co/liter.

11. The method of claim 7 wherein the support is selected from the group consisting of silica, alumina, silica-alumina, titania and mixtures thereof.

12. The method of claim 11 wherein the support has a surface area of 50–500 m²/gm.

* * * * *